United States Patent
Champie

(10) Patent No.: US 10,709,675 B2
(45) Date of Patent: Jul. 14, 2020

(54) NUTRACEUTICAL COMPOSITIONS COMPRISING C60 AND CURCUMIN

(71) Applicant: Max C. Champie, Buena Vista, CO (US)

(72) Inventor: Max C. Champie, Buena Vista, CO (US)

(*) Notice: Subject to any disclaimer, the term of this patent is extended or adjusted under 35 U.S.C. 154(b) by 0 days.

(21) Appl. No.: 16/589,715

(22) Filed: Oct. 1, 2019

(65) Prior Publication Data

US 2020/0188330 A1 Jun. 18, 2020

Related U.S. Application Data

(63) Continuation-in-part of application No. 16/220,890, filed on Dec. 14, 2018.

(51) Int. Cl.
| | |
|---|---|
| *A61K 31/12* | (2006.01) |
| *A61K 31/015* | (2006.01) |
| *A61K 31/122* | (2006.01) |
| *A61K 36/9066* | (2006.01) |
| *A61K 36/185* | (2006.01) |
| *A61K 36/71* | (2006.01) |

(52) U.S. Cl.
CPC ............ *A61K 31/12* (2013.01); *A61K 31/015* (2013.01); *A61K 31/122* (2013.01); *A61K 36/185* (2013.01); *A61K 36/71* (2013.01); *A61K 36/9066* (2013.01)

(58) Field of Classification Search
None
See application file for complete search history.

(56) References Cited

U.S. PATENT DOCUMENTS

| | | |
|---|---|---|
| 8,709,385 B2 | 4/2014 | Tamarkin et al. |
| 10,239,839 B2 | 3/2019 | Kronholm et al. |
| 2008/0038367 A1 | 2/2008 | Saloum |
| 2016/0023826 A1 | 1/2016 | Edwards et al. |

OTHER PUBLICATIONS

Leone, Alessandro. Moringa oleifera Seeds and Oil: Characteristics and Uses for Human Health. Int. J. Mol. Sci. 2016, 17(12), 1-14.*
Gupta, Bhanushree. Thymoquinone. Nutraceuticals, 2016, 1-9.*
CN106692189A translation, Dec. 19, 2019, 1-17.*
Jing Cao et al., Investigation of the Anti-Cataractogenic Mechanisms of Curcumin Through in Vivo and Vitro Studies, BMC Opthamlmology, (2018) 18:48, pp. 1-8.
Xiu-Fen Liu et al., Curcumin, A Potential Therapeutic Candidate for Anterior Segment Eye Diseases: A Review, Frontiers in Pharmacology, Feb. 14, 2017, vol. 8, Article 66, pp. 1-13.
Crystal Y. Usenko et al., Fullerene C.60 Exposure Elicits and Oxidative Stress Response in Embryonic Zebrafish, National Institute of Health, NIH Public Access, May 15, 2008; 229(1), pp. 1-22.
Raghu Pullakhandam et al., Micellarization and Intestinal Cell Uptake of B-Carotene and Lutein from Drumstick Leaves, Journal of Medicinal Food, 2007, pp. 252-257.
Sidney J. Stohs et al., Review of the Safety and Efficacy of Moringa Oleifera, Phytotherapy Research, Mar. 24, 2015, pp. 796-804.

* cited by examiner

*Primary Examiner* — Samantha L Shterengarts
(74) *Attorney, Agent, or Firm* — Fish IP Law, LLP

(57) ABSTRACT

A nutraceutical composition comprising fullerene (e.g., C60), curcumin, and at least one of black seed oil and moringa oil. Preferably, the nutraceutical composition is substantially free of particles having a size greater than 0.2 µm. The nutraceutical composition can be used to prevent and to treat eye conditions (e.g., cataract) by local administration to the eye, oral administration, or both.

17 Claims, No Drawings

NUTRACEUTICAL COMPOSITIONS COMPRISING C60 AND CURCUMIN

CROSS-REFERENCE TO RELATED APPLICATIONS

This application claims priority to, and is a continuation in part (CIP) of, U.S. Utility application Ser. No. 16/220,890, titled "Nutraceutical Compositions Comprising C60 and Cox-2 Inhibitor" by the same inventor, filed on Dec. 14, 2018, which is incorporated herein by reference in its entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is nutraceutical compositions.

BACKGROUND

The following description includes information that may be useful in understanding the present invention. It is not an admission that any of the information provided herein is prior art or relevant to the presently claimed invention, or that any publication specifically or implicitly referenced is prior art.

A cataract is a clouding of the lens in the eye that affects vision. It is caused by proteins in the lens clumping together and preventing light from passing through. The exact cause of clumping is unknown. Researchers suspect that there are several causes of cataract, including smoking, drinking, diabetes, and ultraviolet sunlight. Or, it may be that the protein in the lens just changes from the wear and tear it takes over the years. Currently, surgery is the only effective treatment for cataract by removing the cloudy lens and replacing it with an artificial lens. However, as with any surgery, cataract surgery poses significant risks, including infection and bleeding.

Thus, there is still a need for a non-surgical treatment option for cataract.

DETAILED DESCRIPTION OF THE INVENTION

The inventive subject matter provides composition and methods in which nutraceutical compositions comprising fullerene, curcumin, and at least one of black seed oil and moringa oil, can used to treat an eye condition (e.g., cataract).

Curcumin is the major polyphenol in the spice turmeric. Black seed oil is derived from the seeds of *Nigella sativa*, a small plant that grows in Eastern Europe, Western Asia, and the Middle East. Thymoquinone is the bioactive phytochemical constituent of the seeds oil of *Nigella sativa*. Moringa oil is derived from the seeds of the moringa oleifera tree native to India, Bangladesh and Afghanistan. Buckminsterfullerene is a fullerene with the formula C60.

The contemplated nutraceutical compositions contain fullerene, curcumin, and at least one of black seed oil and moringa oil. In some embodiments, the composition contains black seed oil but not moringa oil. In some embodiments, the nutraceutical composition contains moringa oil but not black seed oil, and optionally, thymoquinone can be added. In some embodiments, the nutraceutical composition contains both moringa oil and black seed oil. In preferred embodiments, the fullerene is C60. In some embodiments, turmeric is used as the source curcumin, which is isolated and purified from turmeric. In some embodiments, the nutraceutical composition contains turmeric. In some embodiments, the nutraceutical composition's active ingredients consist essentially of fullerene, curcumin, and at least one of black seed oil and moringa oil. In some embodiments, the nutraceutical composition's active ingredients consist of fullerene, curcumin, and at least one of black seed oil and moringa oil.

In some embodiments, the nutraceutical composition is a solution or a suspension of small particles having a size no greater than 0.5 µm. In preferred embodiments, the nutraceutical composition is substantially free of particles having a size of greater than 0.2 µm. It is contemplated that this can be achieved by filtering the composition with a filter having a pore size of 0.2 µm. As used herein, "size" refers to the longest distance from one end of a particle to another end of the particle. As applied to a particle with a spherical shape, "size" refers to its diameter.

The inventive subject matter also provides a method of treating an eye condition, by administering a therapeutically effective amount of the nutraceutical composition described herein into an eye, i.e., inside the eyelid, or on the surface of the eyeball, preferably using an eye dropper. In some embodiments, the nutraceutical composition is both delivered into the eye and consumed orally by the patient. In preferred embodiments, the nutraceutical composition to be delivered to the eye comprises moringa oil but not black seed oil, while the nutraceutical composition to be orally administered comprises black seed oil but not moringa oil.

Contemplated eye conditions that can be treated or prevented with the composition and methods described herein include cataract, presbyopia, glaucoma, dry eyes, age-related macular degeneration, and temporal arteritis. Anecdotal evidence from human volunteers has demonstrated that the nutraceutical composition according to teachings herein has unexpected benefits in reversing cataract and restoring eyesight. It is further contemplated that nutraceutical composition described herein can be used to prevent those age-related eye conditions mentioned above.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A nutraceutical composition comprising a fullerene, curcumin, and at least one of black seed oil and moringa oil, wherein the composition is substantially free of particles having a size of greater than 0.2 µm.

2. The nutraceutical composition of claim 1, comprising black seed oil but not moringa oil.

3. The nutraceutical composition of claim 1, comprising moringa oil but not black seed oil.

4. The nutraceutical composition of claim 3, further comprising thymoquinone.

5. The nutraceutical composition of claim 1, comprising both moringa oil and black seed oil.

6. The nutraceutical composition of claim 1, wherein fullerene is C60.

7. The nutraceutical composition in claim 1, further comprising using turmeric as the source of curcumin.

8. A method of treating an eye condition, comprising administering to an eye of a recipient, a first nutraceutical composition comprising a fullerene, curcumin, and at least one of black seed oil and moringa oil.

9. The method in claim 8, wherein the first nutraceutical composition comprises moringa oil but not black seed oil.

10. The method in claim 8, further comprising orally administering to the recipient, a second nutraceutical composition comprising a fullerene, curcumin, and at least one of black seed oil and moringa oil.

11. The method in claim 10, wherein the second nutraceutical composition comprises black seed oil but not moringa oil.

12. The method in claim 11, wherein the first nutraceutical composition comprises moringa oil but not black seed oil.

13. A nutraceutical composition, wherein active ingredients consist essentially of fullerene, curcumin, and at least one of black seed oil and moringa oil.

14. The nutraceutical composition of claim 13, wherein active ingredients consist essentially of fullerene, curcumin, and black seed oil but not moringa oil.

15. The nutraceutical composition of claim 13, wherein active ingredients consist essentially of fullerene, curcumin, and moringa oil but not black seed oil.

16. The nutraceutical composition of claim 13, wherein active ingredients consist essentially of fullerene, curcumin, moringa oil and black seed oil.

17. The nutraceutical composition of claim 13, wherein the composition is substantially free of particles having a size of greater than 0.2 µm.

* * * * *